United States Patent [19]

Lartigue-Peyrou et al.

[11] Patent Number: 4,772,737

[45] Date of Patent: Sep. 20, 1988

[54] HYDROLYSIS OF DIORGANODICHLOROSILANES

[75] Inventors: Francoise Lartigue-Peyrou, Bron; Hugues Porte, Lyon, both of France

[73] Assignee: Rhone-Poulenc Chimie, Courbevoie, France

[21] Appl. No.: 111,578

[22] Filed: Oct. 23, 1987

[30] Foreign Application Priority Data

Oct. 23, 1986 [FR] France ................ 86 14930

[51] Int. Cl.$^4$ ................ C07F 7/08
[52] U.S. Cl. ................ 556/460; 556/459; 556/461
[58] Field of Search ........ 556/460, 459, 461

[56] References Cited

U.S. PATENT DOCUMENTS

| | | | |
|---|---|---|---|
| 3,122,521 | 2/1964 | Pierce | 556/460 X |
| 3,243,410 | 3/1966 | McVannel | 556/460 X |
| 3,360,538 | 12/1967 | Ashby | 556/460 X |
| 3,983,148 | 9/1976 | Reedy et al. | 556/460 |
| 4,348,532 | 9/1982 | Alanko et al. | 556/460 X |
| 4,412,080 | 10/1983 | Williams | 556/460 |
| 4,412,081 | 10/1983 | Williams | 556/460 |
| 4,423,240 | 12/1983 | Yeboah | 556/460 |
| 4,447,630 | 5/1984 | Williams | 556/460 |

Primary Examiner—Paul F. Shaver
Attorney, Agent, or Firm—Burns, Doane, Swecker & Mathis

[57] ABSTRACT

Admixtures of cyclic and linear diorganopolysiloxanes, relatively rich in cyclic species, are produced by hydrolyzing a diorganodichlorosilane, in an aqueous hydrochloric acid medium, in the presence of an effective amount of at least one amphoteric surface-active agent, characteristically at least one compound of the formula:

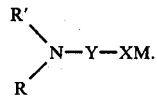

The medium of hydrolysis is facilely separated into an aqueous phase and a cyclic oligomer-enriched siloxane phase essentially devoid of surfactant(s).

12 Claims, No Drawings

HYDROLYSIS OF DIORGANODICHLOROSILANES

BACKGROUND OF THE INVENTION

1. Field of the Invention

The present invention relates to the hydrolysis of organodichlorosilanes in the presence of an amphoteric surface-active agent.

2. Description of the Prior Art

The hydrolysis of organodichlorosilanes, in particular of dimethyldichlorosilane, to produce cyclic and linear polydimethylsiloxanes, has long been known to this art and is described in numerous patents and publications.

Thus, hydrolytic processes in the liquid aqueous phase with production of gaseous HCl are described, for example, in U.S. Pat. No. 2,483,983 and in French Pat. No. 1,584,040.

Furthermore, it too is known to this art to carry out such hydrolyses in the presence of a cationic (U.S. Pat. No. 3,983,148) or anionic surface-active agent (U.S. Pat. Nos. 4,412,080, 4,423,240 and 4,447,630).

In all instances, the surface-active agent is employed for the purpose of increasing the content of cyclic dimethylpolysiloxanes.

According to U.S. Pat. No. 3,983,148, the cationic surface-active agent is a quaternary ammonium salt, protonated amine or protonated quaternary phosphonium salt.

These surface-active agents do, indeed, increase the content of dimethylcyclopolysiloxanes, but they display at least one of the following two disadvantages:

(1) They are not completely insoluble in the polysiloxanes and they are found in excessively high concentrations in the latter, despite repeated washings;

(2) The resulting aqueous emulsion is generally too stable and it is difficult to separate the aqueous phase from the siloxane phase without conducting an additional treatment, for example heating, which may adversely affect the preservation of the cyclic polysiloxanes produced.

While the anionic surfactants described in the aforementioned three U.S. patents are poorly soluble in the siloxane phase and do not display the disadvantage (1), they do indeed exhibit the disadvantage (2) and, in addition, during hydrolysis they exert detrimental influence on the degree of polymerization of the cyclic siloxanes produced. In point of fact, the trimers and tetramers $D_3$ and $D_4$ tend to be converted into their higher homologs $D_5$ and $D_6$, as described, furthermore, in U.S. Pat. No. 4,412,081. This may prove disadvantageous, especially during the separation of the aqueous and siloxane phases. This disadvantage may also exist in the case of the cationic surfactants, as reflected in U.S. Pat. No. 4,556,726. Moreover, the cyclic compounds $D_x$, where x is greater than or equal to 5, are less stable when heated and/or in the presence of an $RSO^-_3$ anion and have a tendency to transform into linear siloxanes.

SUMMARY OF THE INVENTION

Accordingly, a major object of the present invention is the provision of an improved process for the hydrolysis of organodichlorosilanes which ameliorates, conspicuously, those disadvantages and drawbacks to date characterizing the state of this particular hydrolysis/surfactant art, and which improved process permits an appreciable increase in the proportion of cyclic siloxane oligomers produced during the hydrolysis, especially of the tetramer $D_4$.

Briefly, the present invention features a process for the preparation of a mixture of cyclic and linear diorganopolysiloxanes by hydrolysis of diorganodichlorosilanes in an aqueous hydrochloric acid medium, comprising conducting the hydrolysis in the presence of an effective amount of at least one amphoteric surface-active agent, and whereby the content of cyclic siloxanes, particularly of $D_4$, is appreciably increased.

By the expression "appreciably increased" is herein intended an increase of at least 5% by weight of cyclic molecules relative to the weight of cyclic molecules which would have been obtained when carrying out the process in the absence of a surface-active agent.

By an "effective amount" of a surface-active agent is generally intended an amount such that the concentration of the amphoteric surface-active agent in the aqueous phase ranges from between approximately 0.01 to 5% by weight, and preferably from 0.05 to 3% by weight.

DETAILED DESCRIPTION OF THE PREFERRED EMBODIMENTS OF THE INVENTION

More particularly according to the present invention, the amphoteric surface-active agent is most advantageously a compound having the formula:

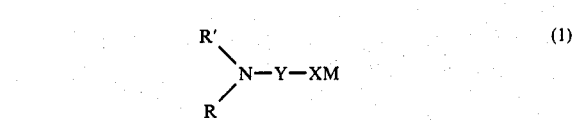

in which R and R', which may be identical or different, are each an alkylaminoalkyl radical, a linear or branched chain $C_1$–$C_{20}$ alkyl radical, or a hydrogen atom, with the proviso that R and R' may form, together with the nitrogen atom from which they depend, a saturated or unsaturated heterocyclic radical containing 1 or 2 nuclei, wherein each nucleus contains from 4 to 6 nuclear atoms, inclusive; X is $COO^-$ or $SO^-_3$; M is a hydrogen atom, an alkali metal, or a tetraalkylammonium group wherein the alkyl radicals are $C_1$–$C_{20}$ alkyl radicals; and Y is a linear or branched chain $C_1$–$C_{20}$ alkylene radical, with the further proviso that at least one of the groups R, R' and Y contains at least 7 carbon atoms.

Exemplary of the R and R' alkyl radicals, representative are methyl, ethyl, n-propyl, n-butyl, n-pentyl, n-octyl and n-decyl radicals.

Exemplary of the single nucleus heterocyclic radicals comprised of R, R' and N, representative are 2H-pyrrolyl, pyridyl, pyrrolidinyl, piperazinyl, Δ2-pyrrolinyl, piperidyl, pyrazolyl, pyrazinyl and imidazolidinyl radicals.

Representative heterocyclic radicals comprised of two nuclei are indolyl, indolinyl and isoindolinyl radicals.

Representative alkali metals are lithium, sodium and potassium.

Exemplary of the preferred surfactants are those compounds of the formulae:

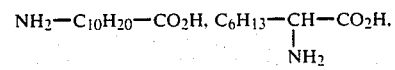

-continued

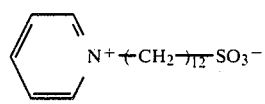

and admixture of compounds of the formula $$R-NH-CH-CH_2-COONa$$
$$\phantom{R-NH-}|$$
$$\phantom{R-NH-}CH_3$$

wherein R is a $C_7$-$C_{16}$ alkyl radical.

The starting material diorganodichlorosilane is typically dimethyldichlorosilane.

However, the use of silanes containing hydrocarbon groups other than the methyl radical is also within the ambit of this invention. In particular, such organic radicals may be identical or different and may be $C_1$-$C_4$ alkyl radicals such as the vinyl radical, and a phenyl, tolyl, xylyl and cycloalkyl radical.

A dilute or saturated aqueous solution containing HCl is advantageously employed as the hydrolysis medium.

The concentration of the HCl in water typically ranges from 20 to 32% by weight, or more, or corresponds, under the temperature and pressure conditions of the hydrolysis, to an aqueous solution saturated with HCl. In this latter case, the HCl formed by hydrolysis is released in gaseous form and may be employed, for example, to produce methyl chloride from the methanol employed subsequently for the synthesis of dimethyldichlorosilane by Rochow direct synthesis.

The medium of hydrolysis always comprises at least two moles of water per mole of silane, generally from 10 to 50 moles of water. The hydrolysis may be carried out continuously or discontinuously at ambient temperature (20° C.) or at a temperature of from 5° C. to 90° C. The hydrolysis is carried out at a pressure equal to or higher than atmospheric pressure with water being continuously or discontinuously added thereto, at least in the continuous process, in order to maintain a constant aqueous phase.

The hydrolysis time preferably ranges from 1 second to 1 hour.

Shorter reaction times are preferred to avoid degradation of the cyclic compounds produced.

After hydrolysis, the aqueous phase is separated from the siloxane phase by any suitable physical technique, typically by gravity separation.

The siloxane phase may be subsequently washed with a basic solution, for example with sodium carbonate or bicarbonate, with sodium hydroxide, or washed merely with water. The various siloxane polymers may then be separated by fractional distillation.

In order to further illustrate the present invention and the advantages thereof, the following specific examples are given, it being understood that same are intended only as illustrative and in nowise limitative. In said examples to follow, all parts and percentages are given by weight.

EXAMPLES 1 TO 4

8 g of various surfactants were added to 720 ml of an aqueous solution at ambient temperature, which was subjected to constant stirring (800 revolutions/min) and saturated with HCl at atmospheric pressure, in a cylindrical glass reactor 10 cm in diameter and 1.3 liters in volume.

The reactor, the temperature of which was maintained by a water bath thermostated at a temperature of from 20° to 30° C., was equipped with a stirring system, a thermometer and a dropping funnel, by means of which 80 g of dimethyldichlorosilane were introduced into the reactor over two seconds and the stirring was maintained for 5 minutes at ambient temperature (25° C.).

At the end of this time period, the reaction mixture was transferred to a second, 3-liter cylindrical reactor, 12 cm in diameter, also equipped with a stirring system and containing water, in order to wash the produced siloxane for 10 minutes. The organic phase was then extracted with toluene and then washed with water until the chloride ions were removed in the wash waters, determined by the absence of turbidity in the silver nitrate test.

The polydimethylsiloxane mixture thus obtained was analyzed by gas phase chromatography after drying over a molecular sieve, using undecane as the internal standard. The results obtained are reported in Table I below:

TABLE I

|  | Example No. |  |  |  |
| --- | --- | --- | --- | --- |
|  | 1 | 2 | 3 | 4 |
| Surfactant(s.) | none | A | B | C |
| Surfactant(s.) concentration (weight %) | — | 1 | 1 | 1 |
| Number of washes | 5 | 8 | 6 | 4 |
| (%) D3 | 0.1 | 0.3 | 0.2 | 0.5 |
| (%) D4 | 43.0 | 48 | 43.5 | 59 |
| (%) D5 | 9.5 | 12.5 | 12 | 17 |
| (%) D6 | 1.5 | 3 | 4 | 2 |
| (Σ) Dx | 55 | 65.5 | 64 | 84 |

Legend:
s. = surfactant
A: $NH_2-C_{10}H_{20}-CO_2H$
B: 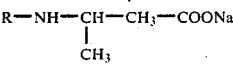
C: mixture of compounds of the formula:
$R-NH-CH-CH_3-COONa$
$\phantom{R-NH-}|$
$\phantom{R-NH-}CH_3$
wherein the alkyl radical R ranged from $C_7$ to $C_{16}$ alkyl, marketed by the Societé Francaise d'Organosynthese under the trademark Cemulcat ® 601.
ΣDx: weight percentage of the cyclosiloxanes with x ranging from 3 to 10 inclusive.

EXAMPLES 5 TO 10

135 g of a solution saturated with HCl (37 to 40% HCl) and variable quantities q of various surface-active agents were introduced into a 500-ml three-necked round flask equipped with a stirrer, a dropping funnel, a thermometer and a temperature controller. 70 g of $Me_2SiCl_2$ were added dropwise over 25 minutes while the temperature was maintained at 20° C. and the stirring maintained constant at 800 revolutions/min. During the reaction time period, the gaseous HCl released was absorbed by means of a running-water trap.

Upon completion of the addition, stirring of the reaction mixture was continued for 5 minutes and then the contents of the flask were transferred into a 250-ml separating funnel. After 10 minutes, when the separation was complete, the siloxane phase was placed again in the round flask, where it was neutralized hot (60° C.) over 15 minutes, while being stirred continuously (800 revolutions/min) with an equal volume of saturated sodium bicarbonate solution.

At the end of this neutralization step, a second gravity separation (10 minutes) produced a neutral and clear siloxane phase, which was analyzed by gas phase chromatography after drying over a molecular sieve.

The results obtained are reported in Table II below, in which:

A, B, C, and ΣDX: same meaning as in Table I.

s. = surfactant.

TABLE II

| | EXAMPLES | | | | | |
|---|---|---|---|---|---|---|
| | 5 | 6 | 7 | 8 | 9 | 10 |
| Nature of s. | none | C | C | A | B | B |
| s. concentration (weight %) in the aqueous phase | none | 0.5 | 1 | 0.5 | 0.5 | 1 |
| (%) D3 | 0.4 | 0.7 | 0.3 | 0.6 | 0.5 | 0.5 |
| (%) D4 | 43.5 | 60.5 | 58.5 | 52.0 | 52.0 | 57.0 |
| (%) D5 | 9.0 | 16.5 | 21.0 | 11.0 | 11.0 | 13.0 |
| (%) D6 | 1.5 | 2.5 | 3.5 | 1.5 | 1.5 | 1.5 |
| (Σ) Dx | 55.0 | 80.5 | 83.5 | 66.0 | 65.5 | 72.0 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of admixture of cyclic and linear diorganopolysiloxanes, comprising hydrolyzing a diorganodichlorosilane in the presence of an amount of at least one amphoteric surface-active agent effective to increase the relative content of cyclic siloxanes in the resulting admixture of hydrolysis.

2. The process as defined by claim 1, wherein the medium of hydrolysis comprises an aqueous solution of hydrochloric acid.

3. The process as defined by claim 2, said amphoteric surface-active agent comprising at least one compound of the formula:

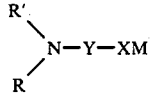
(1)

in which R and R', which may be identical or different, are each an alkylaminoalkyl radical, a linear or branched chain $C_1-C_{20}$ alkyl radical, or a hydrogen atom, with the proviso that R and R' may form, together with the nitrogen atom from which they depend, a saturated or unsaturated heterocyclic radical containing 1 or 2 nuclei, wherein each nucleus contains from 4 to 6 nuclear atoms, inclusive; X is $COO^-$ or $SO^-_3$; M is a hydrogen atom, an alkali metal, or a tetraalkylammonium group wherein the alkyl radicals are $C_1-C_{20}$ alkyl radicals; and Y is a linear or branched chain $C_1-C_{20}$ alkylene radical, with the further proviso that at least one of the groups R, R' and Y contains at least 7 carbon atoms.

4. The process as defined by claim 3, wherein the concentration of said at least one amphoteric surface-active agent ranges from 0.01 to 5% by weight of the aqueous hydrochloric acid medium.

5. The process as defined by claim 3, said amphoteric surface-active agent comprising at least one compound of the formula:

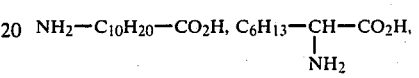

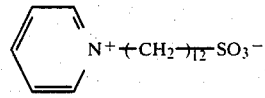

or admixture of compounds of the formula

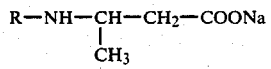

wherein R is a $C_7-C_{16}$ alkyl radical.

6. The process as defined by claim 3, said medium of hydrolysis comprising a saturated aqueous solution of hydrochloric acid.

7. The process as defined by claim 3, said medium of hydrolysis comprising a 20 to 32% by weight concentration of hydrochloric acid in water.

8. The process as defined by claim 3, carried out continuously.

9. The process as defined by claim 3, carried out discontinuously.

10. The process as defined by claim 4, said concentration ranging from 0.05 to 3% by weight.

11. The process as defined by claim 3, said medium of hydrolysis comprising at least 2 moles of water per mole of silane.

12. The process as defined by claim 11, said medium of hydrolysis comprising from 10 to 50 moles of water per mole of silane.

* * * * *